United States Patent
Kurosu et al.

(10) Patent No.: US 8,884,061 B2
(45) Date of Patent: Nov. 11, 2014

(54) COMPOSITIONS AND METHODS OF USE OF ELECTRON TRANSPORT SYSTEM INHIBITORS

(75) Inventors: Michio Kurosu, Windsor, CO (US); Dean Calvin Crick, Fort Collins, CO (US)

(73) Assignee: Colorado State University Research Foundation, Fort Collins, CO (US)

(*) Notice: Subject to any disclaimer, the term of this patent is extended or adjusted under 35 U.S.C. 154(b) by 720 days.

(21) Appl. No.: 12/281,364

(22) PCT Filed: Mar. 2, 2007

(86) PCT No.: PCT/US2007/063122
§ 371 (c)(1),
(2), (4) Date: Sep. 2, 2008

(87) PCT Pub. No.: WO2007/103762
PCT Pub. Date: Sep. 13, 2007

(65) Prior Publication Data
US 2009/0030084 A1    Jan. 29, 2009

Related U.S. Application Data

(60) Provisional application No. 60/779,110, filed on Mar. 3, 2006.

(51) Int. Cl.
| | | |
|---|---|---|
| *A01N 33/02* | (2006.01) | |
| *A61K 31/135* | (2006.01) | |
| *C07C 211/00* | (2006.01) | |
| *C09B 11/02* | (2006.01) | |
| *C07C 215/00* | (2006.01) | |
| *C07C 213/00* | (2006.01) | |
| *C07C 217/00* | (2006.01) | |
| *C07C 321/00* | (2006.01) | |
| *C07C 323/00* | (2006.01) | |
| *C07C 381/00* | (2006.01) | |
| *C07C 217/18* | (2006.01) | |

(52) U.S. Cl.
CPC .................................. *C07C 217/18* (2013.01)
USPC ............................ 564/317; 564/316; 514/651

(58) Field of Classification Search
None
See application file for complete search history.

(56) References Cited

U.S. PATENT DOCUMENTS

| | | | | |
|---|---|---|---|---|
| 2,914,561 A | * | 11/1959 | Schumann et al. | 564/324 |
| 6,034,275 A | * | 3/2000 | Aebi et al. | 564/324 |
| 2004/0132736 A1 | * | 7/2004 | Guzi et al. | 514/252.11 |
| 2005/0096255 A1 | | 5/2005 | Jaworski et al. | |

FOREIGN PATENT DOCUMENTS

GB          919126    *    6/1963

OTHER PUBLICATIONS

GB-919126 Derwent Abstract 1963 pp. 1-18.*
Bohm et al. ChemBioChem, 2004, 5, 637-643.*
Truglio et al. (2003) "Crystal Structure of *Mycobacterium tuberculosis* MenB, a Key Enzyme in Vitamin K2 Biosynthesis" J. Biol. Chem. 278(43):42352-42360.
Weinstein et al. (2005) "Inhibitors of Type II NADH: Menaquinone Oxidoreductase Represent a Class of Antitubercular Drugs" PNAS 102(12):4548-4553.

* cited by examiner

*Primary Examiner* — Clinton Brooks
(74) *Attorney, Agent, or Firm* — Swanson & Bratschun, L.L.C.

(57) ABSTRACT

The invention provides compounds of the formula: or a pharmaceutically acceptable salt thereof, where m, n, $R^1$, $R^2$, $R^3$, $R^4$, $R^5$, $R^6$, $R^7$ are those defined herein. The invention also provides pharmaceutical compositions comprising a compound of the invention, methods for using compounds and/or pharmaceutical compositions of the invention, and methods for synthesizing compounds of the invention.

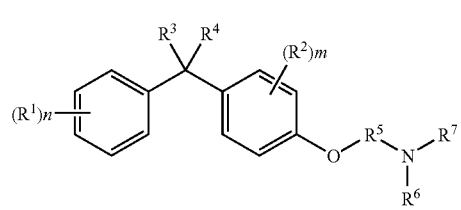

3 Claims, No Drawings

US 8,884,061 B2

COMPOSITIONS AND METHODS OF USE OF ELECTRON TRANSPORT SYSTEM INHIBITORS

CROSS-REFERENCE TO RELATED APPLICATION

This application claims the priority benefit of U.S. Provisional Application Ser. No. 60/779,110, filed Mar. 3, 2006, which is incorporated herein by reference in its entirety.

STATEMENT REGARDING FEDERALLY FUNDED RESEARCH

This invention was made with government support under Grant No. R01AI049151 awarded by the National Institutes of Health. The government has certain rights in the invention.

FIELD OF THE INVENTION

The invention relates to bacteria electron transport system inhibitors and methods for using the same.

BACKGROUND OF THE INVENTION

Infectious diseases remain the largest cause of death in the world today, greater than cardiovascular disease or cancer. In particular, bacterial infection poses one of the major health concerns today, especially by those that are drug resistant.

Most conventional antibiotic drugs act by disrupting the bacteria cell walls or its formation, or by interrupting one or more bacterial enzymes. While such antibiotic drugs have served well in the past, there has been increasing incident of resistance to these types of drugs.

Accordingly, there is a need for antibiotics that have different mode of mechanism.

SUMMARY OF THE INVENTION

One aspect of the invention provides compounds of the Formula:

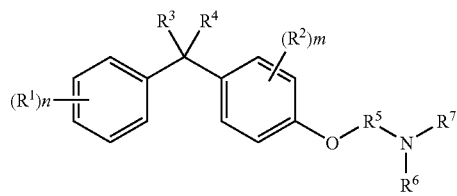

A or a pharmaceutically acceptable salt thereof, where
  m is an integer from 0 to 4;
  n is an integer from 0 to 5;
  each of $R^1$ and $R^2$ is independently halide, haloalkyl (e.g., trifluoromethyl), or $-OR^8$;
  each of $R^3$ and $R^4$ is independently hydrogen or $-OR^8$;
  or $R^3$ and $R^4$ together form $=X$, wherein X is O, S, or $NR^9$;
  $R^5$ is a linker having from about 4 to about 12 atoms each of which is independently selected from the group consisting of C, N, O, S, provided no two heteroatoms are adjacent to one another;
  $R^6$ is hydrogen, alkyl, or $-NR^{10}R^{11}$;
  each of $R^7$ and $R^{10}$ is independently hydrogen, alkyl, aralkyl, alkenyl, or alkynyl;
  each of $R^8$ and $R^9$ is independently hydrogen or alkyl; and
  $R^{11}$ is hydrogen or alkyl.

Other aspects of the invention provide pharmaceutical compositions comprising a compound of Formula A, methods for using compounds and/or pharmaceutical compositions of the invention, and methods for synthesizing compounds of Formula A.

DETAILED DESCRIPTION OF THE INVENTION

Definitions

"Agonist" refers to a compound that enhances the activity of another compound or receptor site.

The term "alkyl" means the monovalent linear saturated hydrocarbon moiety consisting of carbon and hydrogen atoms having from one to twenty, typically from one to twelve, carbon atoms or a branched saturated divalent hydrocarbon moiety of three to twenty, typically three to twelve, carbon atoms. "Lower alkyl" refers to an alkyl group having twelve or less, typically six or less, carbon atoms. Examples of alkyl groups include, but are not limited to, methyl, ethyl, propyl, isopropyl, isobutyl, sec-butyl, tert-butyl, pentyl, n-hexyl, octyl dodecyl, and the like.

The term "alkylene" refers to a saturated linear divalent hydrocarbon moiety of one to twenty, typically one to twelve, carbon atoms or a branched saturated divalent hydrocarbon moiety of three to twenty, often three to twelve, carbon atoms. Exemplary alkylene groups include, hut are not limited to, methylene, ethylene, propylene, butylene, pentylene, hexylene, heptylene, octylene, and the like.

The term "alkenyl" means a linear monovalent hydrocarbon moiety of two to twenty, typically two to twelve, carbon atoms or a branched monovalent hydrocarbon moiety of three to twenty, typically three to twelve, carbon atoms, containing at least one carbon-carbon double bond, e.g., ethenyl, propenyl (i.e., $-CH=CH-CH_3$), allyl (i.e., $-CH_2-CH=CH_2$), and the like.

The term "alkenylene" refers to linear divalent hydrocarbon moiety of two to twenty, typically two to twelve, carbon atoms or branched divalent hydrocarbon moiety of three to twenty, typically three to twelve, carbon atoms having at least one carbon-carbon double bond. Exemplary alkenylene groups include, but are not limited to, ethenylene, propenylene, butenylene, pentenylene, hexenylene, heptenylene, octenylene, nonenylene, and decenylene.

The term "alkynyl" refers to a linear monovalent hydrocarbon moiety of two to twenty, typically two to twelve, carbon atoms or a branched monovalent hydrocarbon moiety of three to twenty, typically three to twelve, carbon atoms containing at least one carbon-carbon triple bond, e.g., ethynyl, propynyl (i.e., $-C\equiv C-CH_3$), propargyl (i.e., $-CH_2-C\equiv CH$), and the like.

The term "alkynylene" refers to linear divalent hydrocarbon moiety of two to twenty, typically two to twelve, carbon atoms or branched divalent hydrocarbon moiety of three to twenty, typically three to twelve, carbon atoms having at least one carbon-carbon triple bond. Exemplary alkynylene groups include, but are not limited to, ethynylene, propynylene, butynylene, pentynylene, hexynylene, heptynylene, octynylene, nonenylene, and decenylene.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aralkyl" refers to a moiety of the formula —$R^b R^c$ where $R^b$ is an alkylene group and $R^c$ is an aryl group as defined herein. Exemplary aralkyl groups include, but are not limited to, benzyl, phenylethyl, 3-(3-chlorophenyl)-2-methylpentyl, and the like.

The terms "halo," "halogen," and "halide," are used interchangeably herein and refer to a substituent fluoro, chloro, bromo, or iodo.

The terms "haloalkyl," "haloalkylene," "haloalkenyl", "haloalkenylene," "haloalkynyl" and "haloalkynylene" refer to alkylene, alkylene, alkenyl, haloalkenylene, alkynyl, and alkynylene, respectively, as defined herein in which one or more hydrogen atoms have been replaced with halogen atom.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Inert organic solvent" or "inert solvent" means the solvent is substantially inert under the conditions of the reaction being described in conjunction therewith. Exemplary inert organic solvents include, but are not limited to, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that, are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium, carbonate and sodium hydroxide.

Typical pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

It should be understood that ail references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula A in vivo when such prodrug is administered to a mammalian subject. Prodrugs of a compound of Formula A are generally prepared by modifying one or more functional group(s) present in the compound of Formula A in such a way that the modification(s) may be cleaved in vivo to release the parent compound. Prodrugs include compounds of Formula A wherein a hydroxy, amino, or sulfhydryl group in a compound of Formula A is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula A. N-acyl derivatives (e.g. N-acetyl) N-Mannich bases, Schiff bases and enaminomes of amino functional groups, oximes, acetals, ketals and enol esters of ketone and aldehyde functional groups in compounds of Formula A, and the like, see Bundegaard, H. "Design of Prodrugs" p1-92, Elesevier. New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, acetyl, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to substantially withstand the desired reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as other limited definitions provided herein, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state;
(ii) inhibiting the disease state, i.e., arresting the development of the disease state or its clinical symptoms; or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Compounds Of The Invention

One aspect of the invention provides a compound of the formula:

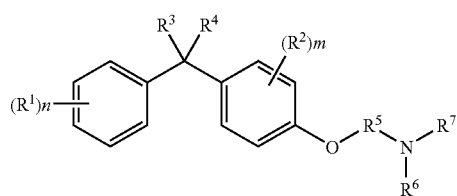

A or a pharmaceutically acceptable salt, thereof, where
m is an integer from 0 to 4;
n is an integer from 0 to 5;
each of $R^1$ and $R^2$ is independently halide, haloalkyl (e.g., trifluoromethyl), or $-OR^8$;
each of $R^3$ and $R^4$ is independently hydrogen or $-OR^8$;
or $R^3$ and $R^4$ together form $=X$, wherein X is O, S, or $NR^9$;
$R^5$ is a linker having from about 4 to about 12 atoms each of which is independently selected from the group consisting of C, N, O, S, provided no two heteroatoms are adjacent to one another;
$R^6$ is hydrogen, alkyl or $-NR^{10}R^{11}$;
each of $R^7$ and $R^{10}$ is independently hydrogen, alkyl, aralkyl, alkenyl, or alkynyl;
each of $R^8$ and $R^9$ is independently hydrogen or alkyl; and
$R^{11}$ is hydrogen or alkyl.

In some embodiments, at least one of $R^3$ and $R^4$ is $-OR^8$, where $R^8$ is that defined herein.

In other embodiments, $R^3$ and $R^4$ together form $=X$, where X is that defined herein. Within these embodiments, in some instances X is O.

In some embodiments, one of $R^3$ and $R^4$ is hydrogen and the other is $-OR^8$, where $R^8$ is that defined herein.

Still in other embodiments, n is 1 to 5. Typically n is 1 or 2.

Yet in other embodiments, $R^1$ is halide. Typically each $R^1$ is independently F, Br or Cl. Often each $R^1$ is independently Br or Cl.

In other embodiments, m is 1.

Still in other embodiments, $R^2$ is hydroxy, alkoxy, F, Cl, or Br. Typically $R^2$ is hydroxy or Cl.

Yet still in other embodiments, $R^5$ is a linker having from about 6 to about 10 atoms each of which is independently selected from the group consisting of C, N, O, S, provided no two heteroatoms are adjacent to one another. It should be noted that when $R^5$ linker has one or more nitrogen atoms, the nitrogen atom is further substituted with $R^{12}$ group, where $R^{12}$ is hydrogen, alkyl, or a nitrogen protecting group. Within these embodiments, in some instances $R^5$ is a linker having 7 or 8 atoms each of which is independently selected from the group consisting of C, N, O, S, provided no two heteroatoms are adjacent to one another. When $R^5$ linker comprises heteroatoms (e.g., N, O, or S), it typically contains one, two or three heteroatoms, more typically one or two heteroatoms, and most often one heteroatom, with the rest of the linker chain atoms being carbon atoms. Within these instances, typically $R^5$ is alkylene, alkenylene, or alkynylene, each of which is optionally substituted with one or more halogens, and wherein one or more carbon, atoms in the chain are optionally replaced with O or N.

Exemplary $R^5$ alkylene groups include, but are not limited to, hexylene, heptylene, octylene, nonylene, decylene, undecylene, and dodecylene. Among these $R^5$ alkylene groups $R^5$ is typically heptylene or octylene. Exemplary $R^5$ alkylene groups having one or more carbon atoms in the chain replaced with O, N, or S include, but are not limited to, the following moiety: $-R^{13}-Z-R^{14}-$, where Z is O, $NR^{15}$ (where $R^{15}$ is hydrogen, alkyl, or a nitrogen protecting group) or S, typically Z is O. Each of $R^{13}$ and $R^{14}$ is independently $C_2-C_8$ alkylene or $C_2-C_8$ haloalkylene, provided the total number of chain atoms in $R^{13}$ and $R^{14}$ is five to twelve, typically six to eight, more typically six or seven, and often seven. In one particular embodiment. $R^{13}$ is $C_4$ alkylene, $R^{14}$ is $C_3$ alkylene, and Z is O.

Exemplary $R^5$ alkenylene groups include, but are not limited to, hexenylene, heptenylene, octenylene, nonenylene, decenylene, undecenylene, and dodecenylene. Among these $R^5$ alkenylene groups $R^5$ is typically heptenylene or octenylene. Exemplary $R^5$ alkenylene groups having one or more carbon atoms in the chain replaced with O, N, or S include, but are not limited to, the following moiety: $-R^{13}-Z-$ $R^{14}$—, where Z is O, $NR^{15}$ (where $R^{15}$ is hydrogen, alkyl, or a nitrogen protecting group) or S, typically Z is O. Each of $R^{13}$ and $R^{14}$ is independently $C_2$-$C_8$ alkylene, $C_2$-$C_8$ haloalkylene, $C_2$-$C_8$ alkenylene, or $C_2$-$C_8$ haloalkenylene, provided the total number of chain atoms in $R^{13}$ and $R^{14}$ is five to twelve, typically six to eight, more typically six or seven, and often seven. And also provided that at least one of $R^{13}$ and $R^{14}$ is $C_2$-$C_8$ alkenylene or $C_2$-$C_8$ haloalkenylene. In one particular embodiment, $R^{13}$ is $C_4$ alkenylene, $R^{14}$ is $C_3$ alkylene, and Z is O.

Exemplary $R^5$ alkynylene groups include, but are not limited to, hexynylene, heptynylene, octynylene, nonynylene, decynylene, undecynylene, and dodecynylene. Among these $R^5$ alkynylene groups $R^5$ is typically heptynylene or octynylene. Exemplary $R^5$ alkynylene groups having one or more carbon atoms in the chain replaced with O, N, or S include, but are not limited to, the following moiety: —R—Z—$R^{14}$—, where Z is O, $NR^{15}$ (where $R^{15}$ is hydrogen, alkyl, or a nitrogen protecting group) or S, typically Z is O. Each of $R^{13}$ and $R^{14}$ is independently $C_2$-$C_8$ alkylene, $C_2$-$C_8$ haloalkylene, $C_2$-$C_8$ alkenylene, $C_2$-$C_8$ haloalkenylene, $C_2$-$C_8$ alkynylene, or $C_2$-$C_8$ haloalkynylene, provided the total number of chain atoms in $R^{13}$ and $R^{14}$ is five to twelve, typically six to eight, more typically six or seven, and often seven. And also provided that at least one of $R^{13}$ and $R^{14}$ is $C_2$-$C_8$ alkynylene or $C_2$-$C_8$ haloalkynylene. In one particular embodiment, $R^{13}$ is $C_4$ alkynylene, $R^{14}$ is $C_3$ alkylene, and Z is O.

In some embodiments, compounds of the invention are of the formula:

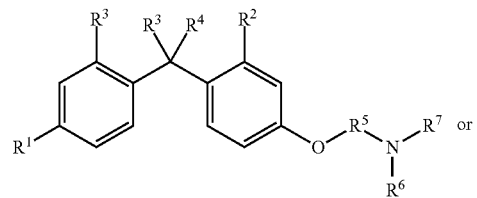

A-1

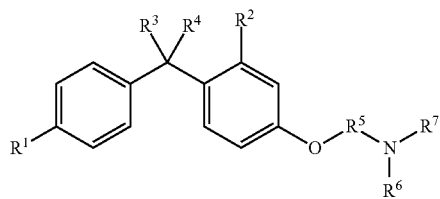

A-2 where $R^1$, $R^2$, $R^3$, $R^4$, $R^5$, $R^6$, and $R^7$ are those defined herein.

In still other embodiments, compounds of the invention include, but are not limited to, combination of various embodiments. For example, in one particular embodiment compounds of the invention include those where $R^3$ is hydrogen, $R^4$ is —$OR^8$, where $R^8$ is hydrogen, n is 2, one of $R^1$ is Br and the other $R^1$ is Cl, m is 1, $R^2$ is hydroxyl $R^5$ is octylene, $R^6$ is hydrogen, and $R^7$ is benzyl. In this manner, a wide variety of compounds are included as specific examples of compounds of the invention. Exemplary compounds of Formula A are listed in Table 1 below.

TABLE 1

Representative compounds of Formula A and the corresponding activities

| Cpd | n | $R^1$ | $R^2$ | $R^3$, $R^4$ | $R^5$ | $R^6$ | $R^7$ |
|---|---|---|---|---|---|---|---|
| 1 | 1 | 4-Br | H | O | —(CH$_2$)$_7$— | Me | Allyl |
| 2 | 1 | 4-Br | H | O | —(CH$_2$)$_8$— | Me | Allyl |
| 3 | 1 | 4-Br | H | H, OH | —(CH$_2$)$_7$— | Me | Allyl |
| 4 | 1 | 4-Br | H | H, OH | —(CH$_2$)$_8$— | Me | Allyl |
| 5 | 1 | 4-Cl | H | O | —(CH$_2$)$_8$— | Me | Allyl |
| 6 | 1 | 4-Cl | H | H, OH | —(CH$_2$)$_8$— | Me | Allyl |
| 7 | 2 | 2,4-Cl | H | O | —(CH$_2$)$_8$— | Me | Allyl |
| 8 | 2 | 2,4-Cl | H | H, OH | —(CH$_2$)$_8$— | Me | Allyl |
| 9 | 1 | 4-Cl | Cl | O | —(CH$_2$)$_8$— | Me | Allyl |
| 10 | 1 | 4-Cl | Cl | H, OH | —(CH$_2$)$_8$— | Me | Allyl |
| 11 | 1 | 4-Cl | Cl | O | —(CH$_2$)$_8$— | Me | —CH$_2$C≡CH |
| 12 | 1 | 4-Cl | Cl | O | —(CH$_2$)$_8$— | Me | —CH$_2$Ph |
| 13 | 1 | 4-Cl | OH | O | —(CH$_2$)$_8$— | Me | Allyl |
| 14 | | | | | —(CH$_2$)$_4$—O—(CH$_2$)$_3$— | | |
| 15 | | | | | —CH$_2$—CH=CH—CH$_2$—O—(CH$_2$)$_3$— | | |
| 16 | | | | | —(CH$_2$)$_5$—C≡C—CH$_2$— | | |
| 17 | | | | | —(CH$_2$)$_4$—O—(CH$_2$)$_3$— | —$NR^{10}R^{11}$ | H |
| 18 | | | | | —CH$_2$—CH=CH—CH$_2$—O—(CH$_2$)$_3$— | —$NR^{10}R^{11}$ | H |
| 19 | | | | | —(CH$_2$)$_5$—C≡C—CH$_2$— | —$NR^{10}R^{11}$ | H |
| 20 | 1 | 4-Cl | 2-Cl | O | —(CH$_2$)$_8$— | Me | Allyl |
| 21 | 1 | 4-Cl | 2-Cl | H, OH | —(CH$_2$)$_8$— | Me | Allyl |
| 22 | 1 | 4-Cl | 2-OH | O | —(CH$_2$)$_8$— | Me | Allyl |

In other embodiments, $R^6$ is alkyl. Within these embodiments, in some instances $R^7$ is alkyl, aralkyl, alkenyl, or alkynyl. In some particular instances, $R^7$ is alkyl, benzyl, allyl, or propargyl.

Yet in other embodiments, $R^6$ is —$NR^{10}R^{11}$, where $R^{10}$ and $R^{11}$ are those defined herein. Within these embodiments, in some instances $R^{10}$ is alkyl, aralkyl, alkenyl, or alkynyl. In some particular instances, $R^{10}$ is alkyl, benzyl, allyl, or propargyl.

Other aspects of the invention provide a method for treating microorganism infection in a subject by administering to a subject in need of such treatment a compound of Formula A or a pharmaceutical composition comprising the same.

Still other aspects of the invention provide methods for making compounds of Formula A and pharmaceutical compositions comprising a compound of Formula A.

Synthesis

Compounds of the invention can be made by a variety of methods depicted in the illustrative examples shown in the Examples section below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the invention can be synthesized, and various modifications to these synthetic reaction schemes can be made and will be suggested to one skilled in the art having referred to the disclosure contained in this disclosure.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reaction described herein typically are conducted under inert atmosphere, at atmospheric pressure, at a reaction temperature range of from about −78° C. to about 230° C., and often conveniently at room (or ambient) temperature, e.g., about 20° C.

Numerous synthetic routes to compounds of the invention will become apparent to those skilled in the art given various synthetic methods disclosed herein. Accordingly, it should be appreciated that the procedures and examples disclosed herein are only exemplary illustrations and are not intended to be limiting. Specific examples of preparing compounds of the present invention are provided in the Examples section. In general, secondary amines were synthesized by the alkylations of polymer-supported secondary amines followed by cleavage of the acid-labile linker as described in detail below. Most of the compounds were characterized using NMR and were purified by silica gel chromatography.

Scheme I below illustrates one exemplary method for producing optionally substituted compounds of Formula A. As shown in Scheme I, Friedel-Crafts coupling of an aryl acyl chloride of Formula I with an anisole of Formula V provided a diaryl ketone compound of Formula II. Removal of the methyl group with HBr provided phenol compound of Formula II. Selective reduction of the ketone carbonyl with sodium borohydride then afforded alcohol compound of Formula IV. Coupling of the phenol hydroxide group of compound of Formula IV with various dibromide compounds then afforded compounds of Formula V, VI, VII, VIII, and IX. Treatment of compounds of Formula V, VI, VII, and VIII with 1,3-propanediol in the presence of a base, e.g., NaH (step e) followed by conversion of the resulting alcohol to bromide with CBr₄ in the presence of PPh₃ (step g) then afforded corresponding bromide compounds of Formula X. For compounds of Formula VIII, the TBS protecting group was first removed with TBAF (step f) prior to converting the alcohol group to bromide with CBr₄ in the presence of PPh₃ (step g) to afford the bromide compound of Formula XI. For compounds of Formula IX there was no need for further functionalization prior to coupling with an amine or a hydrazine compound. Displacement of the bromide group with an amine compound of Formula XII or XIII or with a hydrazino compound of Formula XIV then afforded the desired compounds XV to XX. In this manner, a wide variety of compounds of Formula A was prepared.

Scheme I

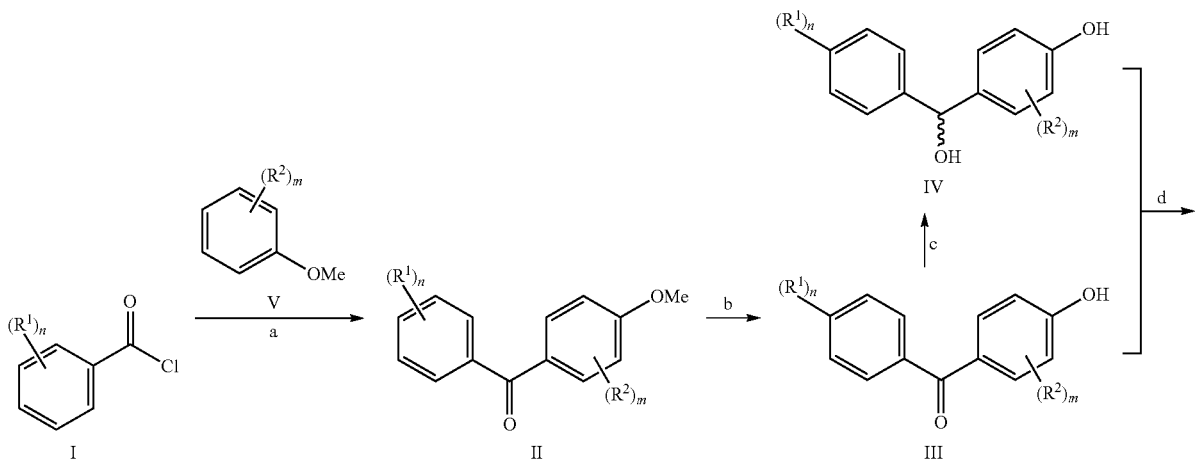

-continued
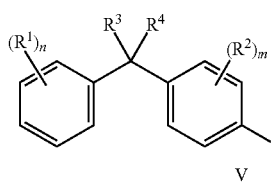
V
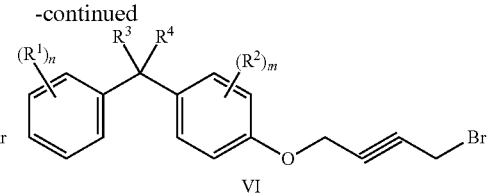
VI
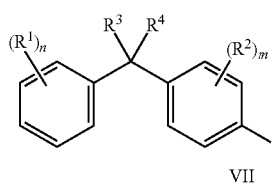
VII
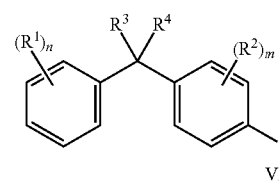
VIII
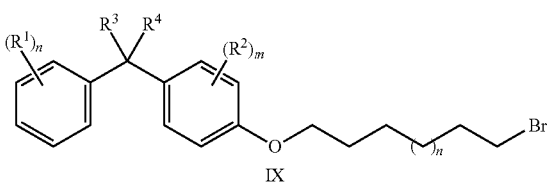
IX
n = 2 or 3
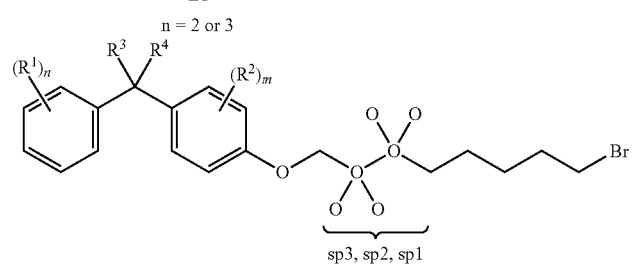
X
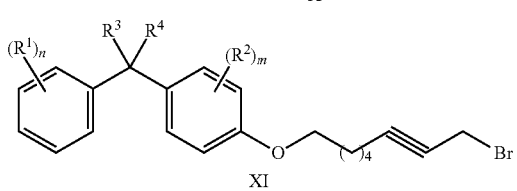
XI
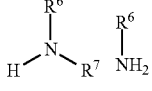
XII
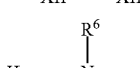
XIII
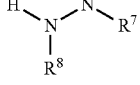
XIV
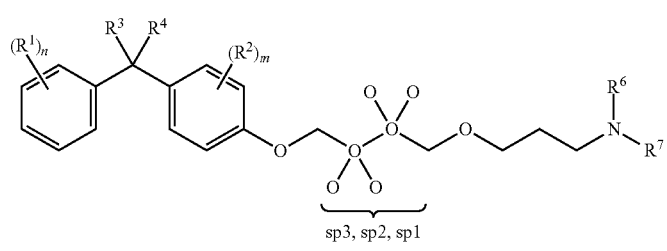
XV
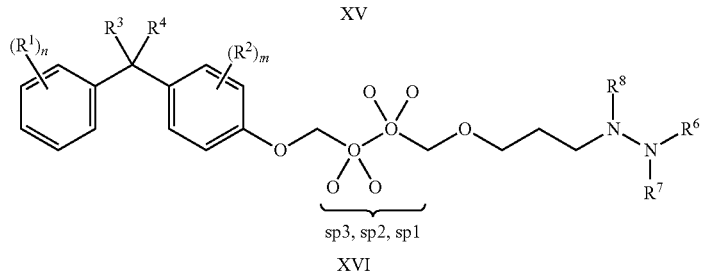
XVI -continued

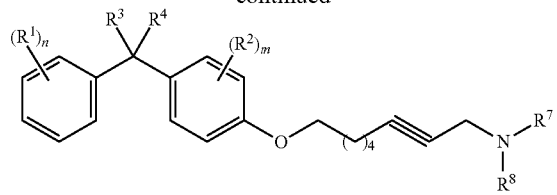

XVII

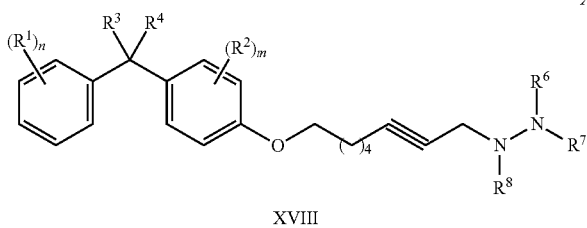

XVIII

XIV
n = 2 or 3

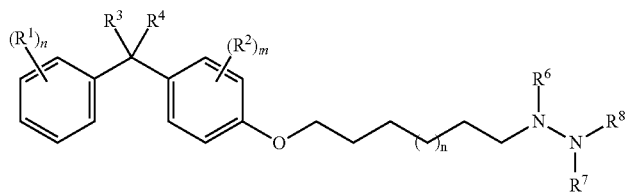

XX
n = 2 or 3

(a) AlCl₃, CH₂Cl₂; (b) 49% HBr, AcOH; (c) NaBH₄, MeOH-THF; (d) (E)-1, 4-dibromobut-2-ene 1, K₂CO₃, DMF; or 1, 4-dibroomobut-2-yne, K₂CO₃, DMF; or 1, 4-dibromobutane, K₂CO₃, DMF; or (8-bromooct-2-ynyloxy)(tert-butyl)dimethylsilane, K₂CO₃, DMF; or 8-dibromooctane or 1, 7-dibromoheptane, K₂CO₃, DMF; (e) 1, 3-propanediol, NaH, DMF; or (f) TBAF, THF for VIII; (g) CBr₄, PPh₃, CH₂Cl₂; skip for IX; (h) XII or XIII or XIV NaHCO₃, DMF.

Scheme II below illustrates another method for preparing compounds of the invention.

Scheme II

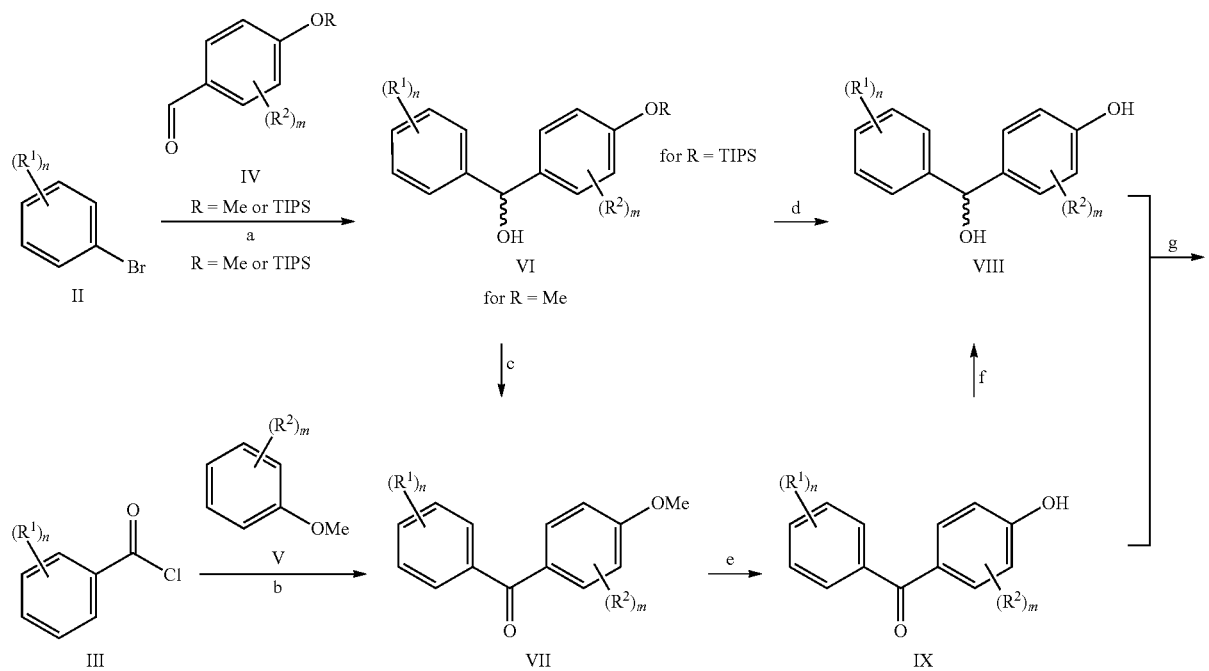

-continued

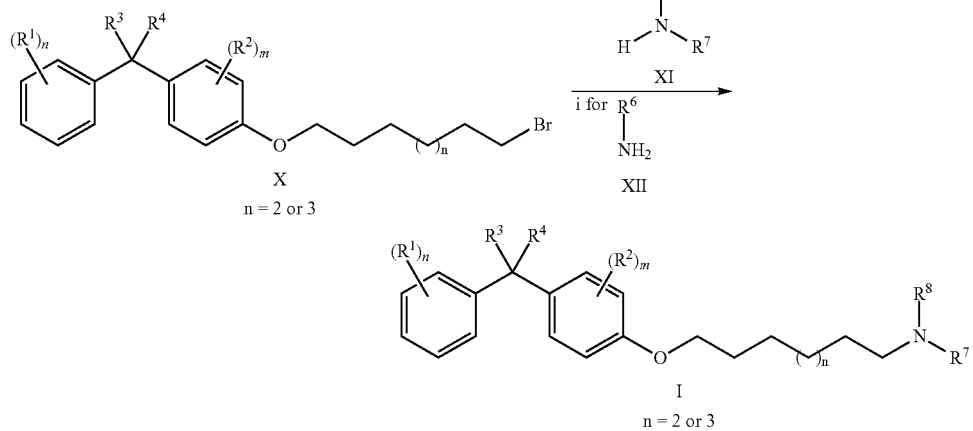

a. nBuLi, THF then IV; b. AlCl₃, V. CH₂Cl₂; c. (COCl)₂, DMSO, CH₂Cl₂, then Et₃N; d. TBAF, THF; e. 49% HBr, AcOH;
f. NaBH₄, MeOH-THF; g. 1, 8-dibromooctane or 1, 7-dibromoheptane, K₂CO₃, DMF; h. XI, NaHCO₃, DMF; i. a) XII, NaHCO₃, DMF. b) PS-TPP, DIAD, R₇-I, THF.
TBAF: tert-butylammoniium fluoride, PS-TPP: triphenylphosphine polymer-bound, DIAD: diisopropyl azocarboxylate The compound VI was synthesized by lithiation of compound II with n-BuLi at −78° C. followed by alkylation of aldehydes IV. The compound. VII was synthesized by Friedel-Crafts acylation of III and V with a stoichiometric amount of AlCl₃ in CH₂Cl₂ at room temperature. The yield of these reactions are typically in the range of 50~95% depending on substituent(s) of aromatic groups. The compound VI (R=Me) was oxidized via a Swern oxidation to provide the compound VII in 90~98% yield. The compound VI (R=TIPS) was desilylated with TBAF to provide the compound VIII in 100% yield. Alternatively, deprotection of the compound VII using 48% HBr in AcOH gave the compound IX in 95% yield. Alkylations of the compounds VIII and IX with 1,8-dibromooctane or 1,7-dibromoheptane gave the desired alkylbromide compound X in over 90% yield. Aminations of X with secondary amines (3 to 5 equivalents) in the presence of NaHCO₃ in DMF afforded compound I in 90~99% yield. The tertiary amine moiety of I could be diversified by aminations of compound X with primary amines followed by alkylation of the resulting secondary amines with triphenylphosphine polymer-bound, diisopropyl azocarboxylate, and alkyliodes, allylbromides, and benzylbromides. Under theses conditions no over-alkylation products were observed.

Dinitrosulfonyl group has been widely utilized as a temporary protecting group of primary amines and N-alkylations of dinitrosulfonamides followed by desufonylation using a primary amine or an alkylthiol in the presence of a tertiary amine provide secondary amines. However, these conditions are not practical for the syntheses of secondary amine building blocks having molecular weight of around 100~250 because of difficult purification of low molecular weight secondary amines from generated by-products and the excess of deprotection reagents. To synthesize low-molecular weight secondary amine building blocks, polymer-supported aldehydes (PS-aldehyde) was introduced in methods of the invention. As illustrated in Scheme III, the amine resins, which were synthesized via a reductive animation (R¹NH₂, NaBH₄, and Ti(Oi-Pr)₄), were subjected to the alkylation reaction using TPP and DIAD (Mitsunobu condition), followed by cleavage of the secondary amine from the polymer-support by using HCl to provide the corresponding secondary amine-HCl salts. Using this procedure a variety of secondary amines were synthesized from primary amines in good yields without a need for chromatographic purification.

Scheme III

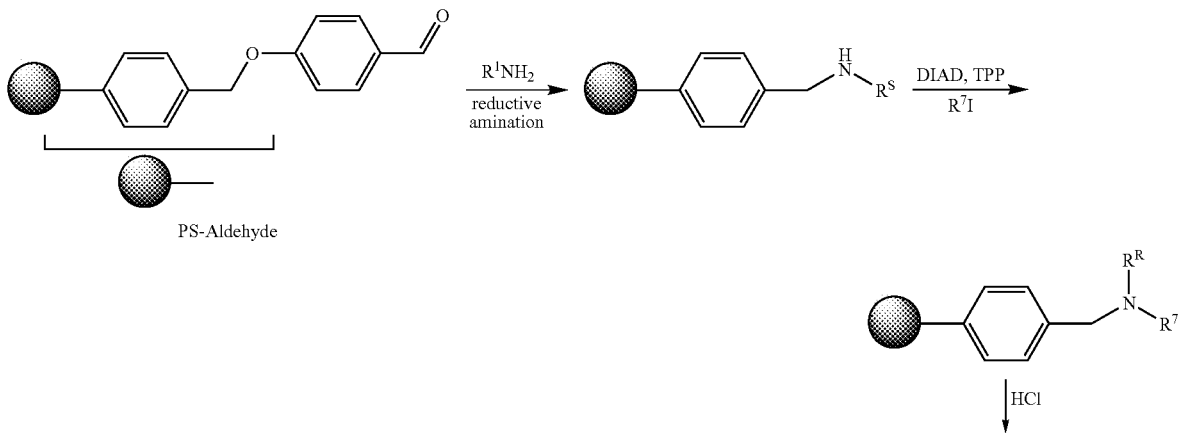

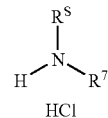

Although Mitsunobu reactions have been utilized in the syntheses of esters, phenol ethers, animations of alcohols, and iodinations of alcohols, previously Mitsunobu conditions have not been applied to the syntheses of tertiary amines. Accordingly, another aspect of the invention provides a method for producing tertiary amines.

While synthesis of compounds of the invention are described with particular reagents, it should be appreciated that one skilled in the art having the disclosure of the present invention can readily determine other suitable acids, bases, solvents, catalysts, oxidizing reagents, and reducing reagents, etc. Similarly, the reaction temperature and duration of the reactions may he adjusted according to the need.

Utility

In prokaryotes, the electron transport chain sometimes utilizes menaquinone (a naphthoquinone) in addition to or instead of ubiquinone (coenzyme Q). *E. coli* utilizes ubiquinone under aerobic conditions, but uses menaquinone under anaerobic conditions. It is believed that some microorganisms including gram-positive bacteria, such as *Mycobacterium tuberculosis* (Mtb), utilizes only menaquinone in the electron transport chain and the menaquinone biosynthesis is believed to be needed for survival of Mtb. Without being bound by any theory, it is believed that oxidative phosphorylation is central component in the production of ATP and the subsequent growth and pathogenesis of some microorganism including gram-positive bacteria, such as Mtb. In contrast, electron transport of humans does not utilize menaquinone. Therefore, inhibitors of menaquinone biosynthesis are believed to be selective drug against microorganisms such as gram-positive bateria including Mtb that is responsible for tuberculosis (TB).

Without being bound by any theory, it is believed that among the menaquinone biosynthesis proteins, menaquinone A (MenA) is a downstream protein that catalyzes the coupling between 1,4-dihydroxy-2-naphthoate (DHNA) and polyprenyldiphosphate through a formal decarboxylative alkylation reaction. Accordingly, it is believed that compounds of the invention are active against pathogens resistant to other clinically useful antibiotics.

Compounds of the invention are menaquinone A inhibitors. Accordingly, compounds of the invention are useful in treating microorganisms that utilize menaquinone A in their electron transport system. Since gram-positive bacteria utilize primarily menaquinone A, if not as the sole mechanism, in electron transport system, it is believed that compounds of the invention are useful in treating gram-positive bacteria infection. For example, Mtb utilizes only menaquinone in the electron transport chain, and the menaquinones are essential for survival of Mtb. Accordingly, compounds of the present invention are useful in treating various bacterial infections in which the bacteria utilizes menaquinone in the electron transport chain. Exemplary bacteria that utilize MenA include *Mycobacterium*, such as *Mycobacterium tuberculosis*. In one embodiment, compounds of the present invention are used to treat multidrug-resistant tuberculosis (MDR-TB) and other pathogenic bacteria which utilize menaquinones in their electron transport systems, in another embodiment, compounds of the present invention are useful as antimycobacterial agents, effective against. Mtb.

Other exemplary gram-positive bacteria include, but are not limited to, *S. aureus* ATCC 29213, *S. aureus* ATCC 43300 (MRSA), VRSA 2441-T0041, VRSA 2441-T0044, MRSA 2441-05104, MRSA 2441-05112, MRSA 2441-05129, MRSA 2441-05223, MRSA 2441-05254, MRSA 2441-05262, *S. epidermidis* ATCC 12228, MRSE 2442-05030, MRSE 2442-05047, MRSE 2442-05053, MRSE 2442-05060, MRSE 2442-05110, MRSE 2442-05118, *E. faecalis* is ATCC 29212, *E. faecalis* is ATCC 51299 (VRE), *E. faecalis* NCTC 12201 (VRE), *E. faecium* ATCC 49224, *E. faecium* NCTC 12203 (VRE) as well as other gram-positive bacteria known to one skilled in the art, see for example. Classification of bacteria according to Bergey's Manual [Bergey's Manual of Systematic Bacteriology. 1st edition. 4 vols. (1984)], Gram-positive Bacteria of medical and commercial importance: (1986) Cocci, endospore-forming and nonsporing rods, mycobacteria, nonfilamentous actinomycetes. Some of the representative gram-positive bacteria include, but are not limited to, the following list of gram-positive bacteria:

Gram-Positive Cocci [Aerobic. Catalase-Positive Genera: *Deinobacter, Deinococcus, Marinococcus, Micrococcus, Planococcus, Saccharococcus, Staphylococcus, Stomatococcus*, Aerotolerant, Catalase-Negative Genera: *Aerococcus Enterococcus, Gemella, Lactococcus, Leuconostoc, Meltssococcus, Pediococcus, Streptococcus* (Pyogenic Hemolytic Streptococci, Oral Streptococci, Enterococci, Lactic Acid Streptococci, Anaerobic Streptococci), *Trichococcus, Vagococcus*, Anaerobic, Catalase-Negative Genera: *Coprococcus, Peptococcus, Peptostreptococcus, Ruminococcus, Sarcina*]: Endospore-Farming Gram-Positive Rods and Cocci [*Amphibacillus, Bacillus, Clostridium, Desulfotomaculum* (also dissimilatory sulfate reducer), *Oscillospira. Sporolactobacillus, Sporosarcina. Sulfidobacillus, Syntrophospora*; Regular, Nonsporing Gram-Positive Rods [*Brochothrix, Carnobacterium, Caryophanon, Erysipelothrix, Kurthia, Lactobacillus, Listeria, Renibacterium*; Irregular, Nonsporing Grain-Positive Rods [*Acetobacterium, Acetogenium, Actinomyces, Aeromicrobium, Agromyces, Arachnia, Arcanobacterium, Arthrobacter, Aureobacterium, Bifidobacterium, Brachybacterium, Brevibacterium, Butyrivibrio* (has thin, gram-positive walls, but stains as negative), *Caseobacter, Cellulomonas, Clavibacter, Coriobacterium, Corynebacterium, Curtobacterium, Dermabacter, Eubacterium, Exigouibacterium, Falcivibrio, Gardnerella* (has thin, gram-positive walls but stains as negative), *Jonesia, Lachnospira* (has thin, grain-positive walls but stains as negative), *Microbacterium, Mobiluncus, Pimelobacter, Propionibacterium, Rarobacter, Rothia, Rubrobacter, Sphaerobacter, Terrabacter, Thermoanaerobacter*; Mycobacteria [Mycobacteriaceae: *Mycobacterium*]; and Nocardioforms [*Intrasporangium, Micropolyspora, Nocardia, Nocardioides, Oerskovia, Promicromonospora, Pseudonocardia, Rhodococcus, Saccharopolyspora*].

Without being bound by any theory, it is believed that compounds of the invention have many advantageous properties compared to many conventional antibacterial drugs. For example, compounds of the invention have enhanced activity against MDR bacteria strains, reduced toxicity, shortened duration of therapy, rapid mycobactericidal mechanism of action, ability to penetrate host cells and exert antimycobacterial effect in the intracellular environment.

Because of their inhibitory activity against MenA, compounds of the invention are also useful research tools for studying the mechanisms of action of these molecules, both in vitro and in vivo. In some instances, compounds of the invention are also useful in treating infections of some gram-negative bacteria, such as *E. Coli* and *K. pneumoniae*.

Bacteria Infection

*Mycobacterium tuberculosis* (Mtb) is the world's number one killer among the infectious diseases. Mtb causes tuberculosis (TB) and is believed to be responsible for nearly two million deaths annually. Estimates indicate that one-third of the world population is infected with latent Mtb. In particular, people who are malnourished or have HIV-AIDS patients are susceptible to TB infection. A chief reason that Mtb persists as a global killer is that existing antibiotics (e.g., isoniazid, rifampicin, pyrazinamide, and ethambutol) require up to 9 months of daily use, making it difficult for people to complete the treatment. Moreover, the emergence multidrug-resistant strains of *Mycobacterium tuberculosis* (MDR-TB) seriously threaten TB control and prevention efforts. It has been estimated that the lifetime risk of developing TB is approximately 10% of infected persons, while the remaining 90% have latent infection with viable bacilli. This 10% rate of TB accounts for the over eight million cases of each year, resulting in two million deaths. As a consequence, the World Health Organization (WHO) has declared in 1993 TB a global public health emergency in an attempt to heighten public and political awareness.

HIV infection is one of the known factors for increasing the risk of TB. At first, HIV increases a person's susceptibility to infection with Mtb. About one third of the 17 million HIV-infected people worldwide were also co-infected with Mtb. An individual co-infected with HIV and Mtb has a 10 times greater risk of developing TB, compared to an individual who is not infected with HIV. On the other hand. TB infection in at) HIV-infected person may allow HIV to multiply more quickly and lead to a more rapid disease progression of AIDS.

Yet the only new TB drugs to become available during the recent decades have been analogs or variations of existing ones. Many first-line antituberculosis agents require activation by bacterial enzyme(s) and detailed mechanisms of action have not yet been determined. Thus, no rational modification of first-line anti-TB agents for MDR-TB has been established.

The recommended treatment of TB is Directly Observed Therapy Short-course (DOTS), which uses a combination of drugs with isoniazid and rifampin taken over 6 months, supplemented with pyrazinamide for the first 2 months, and addition of ethambutol when isoniazid resistance is suspected. DOTS is generally successful, even though the treatment may need to be extended, sometimes to as long as 2 years, in order to fully cure the patient of infectious bacteria. However, poor compliance with such a long, complex and unpleasant combination of drugs results in a significant treatment failure rate. Worse still, resistance may emerge to these first-line agents, and thereafter to a wide range of second-line anti-mycobacterials. Not only are MDR-TB strains difficult to treat but these strains are also life threatening, sometimes resulting in a high mortality rate in a short period of time. In general, treating individuals infected with MDR-TB is expensive, intolerable in toxicity, and frequently unsuccessful. Currently, treatment of drug susceptible TB costs about $2,000 per patient, whereas the cost increases to as much as $250,000 per case for MDR-TB. Presently, there is no standard optimal antimicrobial therapy in AIDS patients and no single agent that is active against both infections.

Even where DOTS has been established, if the MDR rate locally is high, first line drugs alone give an unacceptably low rate. Moreover, if the patient remains ill the transmission rate is increased. Clinical responses of MDR-TB patient to first line drug have been poor, and in some cases there is no response at all. Second line drugs (e.g., amikacin, cycloserine, ethionimide, kanamycin capreomycin, ofloxacin) are often poorly effective and tolerated.

Compounds of the invention are active against Mtb as well as MDR-TB, Thus, compounds of the invention are useful in treating both Mtb as well as MDR-TB. Moreover, since compounds of the invention are active against any microorganism that utilizes menaquinone A in its electron transport system, compounds of the invention are useful in treating infection of any microorganism that utilizes menaquinone A in its electron transport system.

In some embodiments, compounds of the invention are useful in inhibiting biosynthesis of menaquinone A.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present, invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and it reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may he comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methyl cellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain, formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; aid mouthwashes comprising the active ingredient in a suitable liquid carrier.

The compounds of the present invention may be formulated for nasal administration. The solutions or suspensions are applied directly to the nasal cavity by conventional means, for example, with a dropper, pipette or spray. The formulations may he provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can he formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one).

Sustained release delivery systems are inserted subcutaneously into the subdermal layer by surgery or injection. The subdermal implants encapsulate the compound in a lipid soluble membrane, e.g., silicone rubber, or a biodegradable polymer, e.g., poly lactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Additional objects, advantages, and novel features of this invention will become apparent to those skilled in the art upon examination of the following examples thereof which are not intended to be limiting.

EXAMPLES

General Procedures and Methods: $^1$H NMR spectra were recorded on a Varian Inova 500, Varian Mercury 400, or Varian Mercury 300 spectrometer. $^{13}$C NMR spectra were recorded at 100 MHz or 125 MHz. Chemical shifts were reported in parts per million (ppm). The residual solvent peak was used as an internal reference. Fast atom bombardment (FAB) mass spectra were obtained with 3-nitrobenzyl alcohol or glycerol as the matrix. Sodium iodide was added when indicated. Chemical ionization (CI) mass spectra were obtained with ammonia as the reagent gas. Electrospray ionization experiments were performed on Micromass Inc. Platform II Atmospheric Pressure Ionization Mass Spectrometer. Infrared spectra were obtained as films on sodium chloride plates. Analytical thin layer chromatography (TLC) was performed with E. Merck precoated TLC plates, silica gel 60F-254, layer thickness 0.25 mm. Preparative thin layer chromatography (PTLC) separations were performed on E, Merck precoated TLC plates, silica gel 60F-254, layer thickness 0.25 or 0.50 mm. Flash chromatography separations were performed on E. Merck kieselgel 60 (230-400) mesh silica gel.

Reagents and solvents are commercial grade and were used as supplied, with the following exceptions, A bulk THF was purified through $Al_2O_3$ column (solvent purification system) and distilled over $LiAlH_4$. Ether and dichloromethane were purified by solvent purification systems. All reactions were conducted under nitrogen atmosphere. Reaction vessels were flame-dried or oven-dried and cooled under an inert atmosphere.

Example 1

Synthesis of (4-(8-(allyl(methyl)amino)octyloxy)-2-hydroxphenyl)(4-chlorophenyl)methanone To a stirred solution of 4-chlorobenzoyl chloride (1.0 g, 5.8 mmol) and 1,3-dimethoxybenzene (788.5 mg, 5.8 mmol) in $CH_2Cl_2$ (150 mL) at 0° C. was added $AlCl_3$ (841.5 mg, 6.4 mmol). The reaction mixture was warmed to room temperature. After 12h the reaction mixture was poured into aq. $NaHCO_3$ and extracted with $CH_2Cl_2$ (twice). The combined extracts were washed with brine, dried over $Na_2SO_4$, and concentrated in vaccuo to provide a 1:1 mixture of(4-chlorophenyl)(2-hydroxy-4-methoxyphenyl)methanone and (4-chlorophenyl)(2,4-dimethoxyphenyl)methanone. Purification by silica gel chromatography provided methoxyphenyl)methanone (650 mg, 2.5 mmol) and (4-chlorophenyl)(2,4-dimethoxyphenyl)methanone(700 mg, 2.5 mmol). The combined molecules (2.7 g) were dissolved in AcOH (50 mL) and 49% HBr (50 mL) was added. After 12h at 90° C. all volatiles were evaporated in vaccuo to afford (4-chlorophenyl)(2,4-dihydroxyphenyl)methanone in quantitative yield. Without purification this was subjected to alkylation with 1,8-dibromooctane (4.0 g, 14.7 mmol) and $K_2CO_3$ (2.0 g, 14.7 mmol) in DMF (50 mL). After 12 h the reaction mixture was diluted with water (150 mL) and the water phase was extracted with EtOAc (twice). The combined organic phase was washed with brine, dried over $Na_2SO_4$, and concentrated in vaccuo to give the crude product. Purification by silica gel chromatography provided (4-(8-bromooctyloxy)-2-hydroxyphenyl)(4-chlorophenyl)methanone(1.9 g, 4.4 mmol). To a stirred solution of (4-(8-bromooctyloxy)-2-hydroxyphenyl)(4-chlorophenyl)methanone (1.9 g, 4.4 mmol) in THF (25 mL) was added N-methylprop-2-en-1-amine (938.1 mg, 13.2 mmol) and $NaHCO_3$ (13.2 mmol). After 36h at room temperature the reaction mixture was filtered through a glass-filter. The filtrate was evaporated in vaccuo. Purification by silica gel chromatography provided (4-(8-(allyl(methyl)amino)octyloxy)-2-hydroxyphenyl)(4-chlorophenyl)methanone (1.8 g, 1.9 mmol); $^1$H-NMR (300 MHz, $CDCl_3$) 12.6 ppm (s, 1H) , 7.64 (d, J=9.6 Hz, 2H), 7.60-7.48 (m, 3H), 6.59 ( s, 1H), 6.45 (d, J=9.6 Hz, 1H), 6.05-5.84 (m, 1H), 5.39-5.12 (m, 2H), 4.05 (t, J=7.7 Hz, 2H), 3.21-2.99 (m, 2H), 2.51-2.11 (m, 7H), 1.92-1.80 (m, 2H), 1.79-1.21(m, 8H); $^{13}$C-NMR (75 MHz, $CDCl_3$) 196.3 ppm, 162.5, 138.1, 137.8, 134.2, 132.3, 131.7, 128.5, 110.9, 101.8, 68,8, 60.4, 57.0. 43.8, 29.6, 29.3, 27.3, 28.1; ESI-MS calcd for $C_{25}H_{33}ClNO_3$ [M+H+]: 430.2. found 430.2.

Example 2

Synthesis of (4-8-(allyl(methyl)amino)octyloxy)-2-chlorophenyl)(4-chlorophenyl)methanol To a stirred solution of 4-chlorobenzoyl chloride (1.0 g, 5.8 mmol) and 1-chloro-3-methoxybenzene(823.7 mmol) in $CH_2Cl_2$ (150 mL) at 0° C. was added $AlCl_3$ (841.5 mg, 6.4 mmol). The reaction mixture was warmed to room temperature. After 12h the reaction mixture was poured into aq. $NaHCO_3$ and extracted with $CH_2Cl_2$ (twice). The combined extracts were washed with brine, dried over $Na_2SO_4$, and concentrated in vaccuo to provide the crude product. Purification by silica gel chromatography provided (2-chloro-4-methoxyphenyl)(4-chlorophenyl)methanone(1.1 g, 4.1 mmol). (2-Chloro-4-methoxyphenyl)(4-chlorophenyl) methanone was dissolved in AcOH (60 mL) and 49% HBr (60 mL) was added. After 12h at 90° C. all volatiles were evaporated in vaccuo to afford (4-chlorophenyl)(2,4-dihydroxyphenyl)methanone in quantitative yield. This was dissolved in MeOH (30 mL) and THF (6 mL) and cooled to 0° C. Into the reaction mixture $NaBH_4$ (235.5 mg, 6.2 mmol) was added. After 30 minutes the reaction was quenched with aq. $NH_4Cl$ and extracted with EtOAc. The combined extracts were washed with brine, dried over $Na_2SO_4$, and concentrated in vaccuo. Without purification this was subjected to alkylation with 1,8-dibromoocatane (3.3 g, 12.3 mmol) and $K_2CO_3$ (1.7 g, 12.3 mmol) in DMF (45 mL). After 12h the reaction mixture was diluted with water (150 mL) and water phase was extracted with EtOAc (twice). The combined organic phase was washed with brine, dried over $Na_2SO_4$, and concentrated in vaccuo to give the crude product. Purification by silica gel chromatography provided (4-(8-bromooctyloxy)-2-chlorophenyl)(4-chlorophenyl)methanol (1.6 g, 3.5 mmol). To a stirred solution of (4-(8-bromooctyloxy)-2-chlorophenyl)(4-chlorophenyl)methanol (1.6 g, 3.5 mmol) in THF (25 mL) was added N-methylprop-2-en-1-amine (746 mg, 10.5 mmol) and $NaHCO_3$ (11.0 mmol). After 36h at room temperature the reaction mixture was filtered through a glass-filter. The filtrate was evaporated in vaccuo. Purification by silica gel chromatography provided (4-(8-(allyl(methyl)amino)octyloxy)-2-chlorophenyl)(4-chlorophenyl)methanol (1.5 g, 3.3 mmol); $^1$H-NMR (300 MHz, $CDCl_3$); 7.29-7.17 ppm (m, 5H), 6.84 (d, J=10.1 Hz, 1H), 6.74 (s, 1H), 5.98-5.80 (m, 2H), 5.31-5.15 (m, 2H), 3.85 (t, J=7.6 Hz, 2H), 3.20-3.08 (m, 2H), 2.58-2.40 (m, 2H), 2.35 (s, 3H), 1.77-1.45 (m, 4H), 1.32-1.15 (m, 8H); $^{13}$C—NMR (75 MHz, $CDCl_3$) 156.3 ppm, 138.3, 134.2, 131.8, 130.0, 129.6, 129.3, 116.2, 74.5, 68.8, 60.4, 43.8, 57.0, 29.6, 29.3, 28.1, 27.3, 25.9; ESI-MS calcd for $C_{25}H_{34}Cl_2NO_2$ [M+H]$^+$: 450.2. found 450.2.

Example 3

Synthesis of (4-(8-(allyl(methyl)(amino)octyloxy)phenyl)(4-chlorophenyl)methanol To a stirred solution of 1-bromo-4-chlorobenzene (1.0 g, 5.3 mmol) at −78° C.

in THF (30 mL) was added n-BuLi (1.6 M. 5.8 mmol). After 30 minutes 4-(triisopropylsilyloxy)benzaldehyde (1.5 g, 5.3 mmol) in THF (2 mL) was added into the reaction mixture. The reaction mixture was warmed to room temperature and quenched with aq. $NH_4Cl$. The water phase was extracted with EtOAc and the combined extracts were washed with brine, dried over $Na_2SO_4$, and concentrated in vaccuo to provide the crude product. Purification by silica gel chromatography provide (4-chlorophenyl)(4-(triisopropylsilyloxy)phenyl)methanol (1.7 g, 4.2 mmol). (4-Chlorophenyl)(4-(triisopropylsilyloxy)phenyl)methanol (1.7 g, 4.2 mmol) was dissolved in THF (5 mL) and TBAF (1.0 M, 6.0 mmol) was added. After 15 minutes, the reaction mixture was quenched with MeOH (10 mL), concentrated, and the residue was purified by silica gel chromatography to afford 4-((4-chlorophenyl)(hydroxy)methyl)phenol (963.1 mg, 4.1 mmol). This was subjected to alkylation with 1,8-dibromooctane (3.3 g, 12.3 mmol) and $K_2CO_3$ (1.7 g, 12.3 mmol) in DMF (45 mL). After 12h the reaction mixture was diluted with water (150 mL) and water phase was extracted with EtOAc (twice). The combined organic phase was washed with brine, dried over $Na_2SO_4$, and concentrated in vaccuo to give the crude product. Purification by silica gel chromatography provided (4-(8-bromooctyloxy)phenyl)(4-chlorophenyl)methanol (1.6 g, 3.7 mmol).

To a stirred solution of 4-(8-bromooctyloxy)phenyl)(4-chlorophenyl)methanol (1.6 g, 3.7 mmol) in THF (25 mL) was added N-methylprop-2-en-1-amine (746 mg, 10.5 mmol) and $NaHCO_3$ (11.0 mmol). After 36h at room temperature the reaction mixture was filtered through a glass-filter. The filtrate was evaporated in vaccuo. Purification by silica gel chromatography provided (4-(8-(allyl(methyl)amino)octyloxy)phenyl)(4-chlorophenyl)methanol(1.4 g, 3.3 mmol); $^1$H-NMR (300 MHz, $CDCl_3$); 7.25-7.11 ppm (m, 6H), 7.74 (d, J=9.8 Hz, 2H), 5.91-5.73 (m, 1H), 5.65 (s, 1H), 5.20-5.05 (m, 2H), 3.60 (t, J=7.5 Hz, 2H), 3.09 (m, 2H), 2.40-2.29 (m, 2H), 2.21 (s, 3H), 1.71-1.60 (m, 2H), 1.51-1.09 (m, 10H): $^{13}$C-NMR (75 MHz, $CDCl_3$) 154.9 ppm, 138.3, 134.2, 131.8, 130.0, 129.6, 129.3, 128.8, 116.2, 114.9, 68.8, 60.4, 57.0, 43.8, 29.6, 29.6, 29.3, 28.1, 27.3, 25.9; ESI-MS calcd for $C_{25}H_{35}ClNO_2$ [M+H]$^+$: 416.2. found 416.3.

Example 4

4-(8(Allyl(methyl)amino)octyloxy)phenyl)(2,4-dichlorophenyl)methanol

This compound was prepared using the procedure similar to Example 3. $^1$H-NMR (300 MHz, $CDCl_3$): 7.29-7.17 ppm (m, 5H), 6.84 (d, J=10.1 Hz, 1H), 6.74 (s, 1H), 5.98-5.80 (m, 2H), 5.31-5.15 (m, 2H), 3.85 (t, J=7.6 Hz, 2H), 3.20-3.08 (m, 2H), 2.58-2.40 (m, 2H), 2.35 (s, 3H), 1.77-1.45 (m, 4H), 1.32-1.15 (m, 8H); $^{13}$C-NMR (75 MHz, $CDCl_3$) 154.8 ppm, 137.2, 134.9, 134.2, 133.2, 131.9, 130.9, 130.0, 128.8, 127.4, 116.2, 114.9, 68.2, 60.4, 57.0, 43.8, 29.6, 29.3, 28.1, 27.3, 25.9; ESI-MS calcd for $C_{25}H_{34}Cl_2NO_2$ [M+H]$^+$: 450.2, found 450.2.

Example 5

4-(8-(Allyl(methyl)amino)octyloxy)-2-chlorophenyl)(4-chlorophenyl)methanone

This compound was prepared using the procedure similar to Example 3. $^1$H-NMR (300 MHz, $CDCl_3$): 7.79 ppm (d, J=9.6 Hz, 2H), 7.48 (d, J=9.6 Hz, 2H), 7.06-7.24 (m, 6H), 7.03 (s, 1H), 6.9(d, J=10.2 Hz, 1H), 4.08 (t,7.8 Hz, 2H), 3.60 (s, 2H), 2.48-2.40 (m, 2H), 2.28 (s, 3H), 1.95-1.80 (m, 2H), 1.72-1.38 (m, 10H); $^{13}$C-NMR(75 MHz, $CDCl_3$) 196.3 ppm, 162.5, 138.0, 137.8, 135.6, 134.2, 131.7, 133.2, 128.5, 116.2, 114.9, 112.2, 68.9, 60.4, 57.0, 43.8, 29.6, 29.3, 28.1, 27.3, 25.9; ESI-MS calcd for $C_{25}H_{32}Cl_2NO_2$ [M+H]$^+$: 448.2, found 448.1.

Example 6

(4-(8-(Allyl(methyl)amino)octyloxy)phenyl)(2,4-dichlorophenyl)methanone

This compound was prepared using the procedure similar to Example 3. $^1$H-NMR (300 MHz, $CDCl_3$): 7.79 ppm (d, J=9.8Hz, 2H), 7.27 (d, J=9.8 Hz, 2H), 7.20 (d, J=10.2 Hz, 1H), 7.02 (s, 1H), 6.94 (d, J=10.2 Hz, 1H), 6.30-6.11 (m, 1H), 5.67-5.50 (m, 2H), 4.4 (t, J=7.8 Hz, 2H), 3.79-3.55 (m, 2H), 3.19-2.82 (m, 2H), 2.78 (s, 3H), 2.05-1.80 (m, 4H), 1.60-1.28 (m, 8H); $^{13}$C-NMR (75 MHz, $CDCl_3$) 196.4 ppm, 161.1, 139.4, 136.4, 134.5, 134.2, 133.1, 131.3, 130.9, 130.1, 126.9, 116.2, 114.1, 68.8, 60.4, 57.0, 43.8, 29.6, 29.3, 28.1, 27.3, 25.9; ESI-MS calcd for $C_{25}H_{32}Cl_2NO_2$ [M+H]$^+$: 448.2. found 448.1.

Example 7

(4-(8-(Allyl(methyl)amino)octyloxy)phenyl)(4-chlorophenyl)methanone

This compound was prepared using the procedure similar to Example 3. $^1$H-NMR (300 MHz, $CDC_3$): 7.91-7.63 ppm (m, 4H), 7.58 (d, J=9.8 Hz, 2H), 7.12 (d, J=9.8 Hz, 2H), 6.18-5.87 (m, 1H), 5.78-5.52 (m, 2H), 418 (t, J=7.6 Hz, 2H) , 3.82-3.71 (m, 2H), 3.22-3.02 (m, 2H), 2.86 (s, 3H), 2.00-1.41 (m, 12H); $^{13}$C-NMR (75 MHz, $CDCl_3$) 196,3 ppm. 161.3, 138.0, 137.8, 134.2, 134.2, 131.7, 131.3, 128.5, 116.2, 114.1, 68.8, 60.4, 57.0, 43.8, 29.6, 29.3, 28.1, 27.3, 25.9; ESI-MS calcd for $C_{25}H_{33}ClNO_2$ [M+H]$^+$: 414.2. found 414.1.

Example 8

(4-(8-(Allyl(methyl)amino)octyloxy)phenyl))4-bromophenyl)methanone

This compound was prepared using the procedure similar to Example 3. $^1$H-NMR (300 MHz, CDCl$_3$): 7.92-7.63 ppm (m, 4H), 7.48 (d, J=9.8 Hz, 2H), 7.12 (d, J=9.8 Hz, 2H), 6.18-5.87 (m, 1H), 5.78-5.52 (m, 2H), 4.18 (t, J=7.6 Hz, 2H), 3.82-3.71 (m, 2H), 3.22-3.02 (m, 2H), 2.86 (s, 3H), 2.00-1.41 (m, 12H); $^{13}$C-NMR (75 MHz, CDCl$_3$) 196.3 ppm, 161.1, 138.7, 137.8, 134.2, 134.2, 131.7, 131.3, 128.5, 116.2, 114.1, 68.8, 60.4, 57.0, 43.7, 29.6, 29.3, 28.1, 27.3, 25.9; ESI-MS calcd for $C_{25}H_{33}BrNO_2$ [M+H]: 458.2. found 458.2.

Example 9

(4-(7-(allyl(methyl)amino)heptyloxy)phenyl)(4-bromophenyl)methanone

This compound was prepared using the procedure similar to Example 3. $^1$H-NMR (300 MHz, CDCl$_3$): 7.92-7.63 ppm (m, 4H), 7.48 (d, J=9.8 Hz, 2H), 7.12 (d, J=9.8 Hz, 2H), 6.18-5.87 (m, 1H) 5.78-5.52 (m, 2H), 4.18 (t, J=7.6 Hz, 2H), 3.82-3.71 (m, 2H), 3.22-3.02 (m, 2H), 2.86 (s, 3H), 2.00-1.41 (m, 10H); $^{13}$C-NMR (75 MHz, CDCl$_3$) 196.3 ppm, 161.1, 138.7, 1.37.8, 134.2, 134.2, 131.7, 131.3, 128.5, 116.2, 114.1, 68.8, 60.4, 57.0, 43.7, 29.6, 29.3, 28.0, 25.9: ESI-MS calcd for $C_{24}H_{31}BrNO_2$ [M+H]: 444.2. found 444.1.

Example 10

(2-Chloro-4-(8-(methyl(prop-2-ynyl)amino)octyloxy)phenyl)(4-chlorophenyl)methanone This compound was prepared using the procedure similar to Example 3. $^1$H-NMR (300 MHz, CDCl$_3$): 7.78 ppm (d, J=9.7 Hz, 2H), 7.45 (d, J=9.7 Hz, 2H), 7.20 (d, J=10.1 Hz, 1H), 7.02 (s, 1H), 6.91(d, J=10.1 Hz, 1H), 4.05 (t, J=7.6 Hz, 2H), 3.21 (s, 2H), 2.48 (t, J=7.8 Hz, 2H), 2.38(s, 3H), 2.29(s, 1H), 1.92-1.80 (m, 2H), 1.60-1.31 (m, 10H); $^{13}$C-NMR (75 MHz, CDCl$_3$) 196.3 ppm, 162.5, 138.0, 137.8, 135.6, 132.3, 131.7, 128.5, 128.0, 116.2, 114.9, 112.2, 78.0, 70.9, 55.7, 42.5, 29.6, 29.3, 27.3, 27.1, 25.9; ESI-MS calcd for $C_{25}H_{30}Cl_2NO_2$ [M+H]$^+$: 446.2. found 446.2.

Example 11

(4-(8-(Benzyl(methyl(amino)octyloxy)-2-chlorophenyl)(4-chlorophenyl)methanone

This compound was prepared using the procedure similar to Example 3. $^1$H-NMR (300 MHz, CDCl$_3$): 7.79 ppm (d, J=9.6 Hz, 2H), 7.48 (d, J=9.6 Hz, 2H), 7.06-7.24 (m, 6H), 7.03 (s, 1H), 6.91 (d, J=10.2 Hz, 1H), 4.08 (t, J=7.8 Hz, 2H), 3.60 (s, 2H), 2.48-2.40 (m, 2H), 2.28 (s, 3H), 1.95-1.80 (m, 2H), 1.72-1.38 (m, 10H); $^{13}$C-NMR (75 MHz, CDCl$_3$) 196.3 ppm, 162.5, 138.0, 137.8, 135.6, 135.5, 132.3, 131.7, 128.5, 128.4, 128.3, 128.0, 127.3, 116.2, 114.9, 112.2, 68.8, 62.9, 56.5, 43.3, 29.6, 29.3, 27.3, 27.1, 25.9; ESI-MS calcd for $C_{29}H_{34}Cl_2NO_2$ [M+H]$^+$: 498.2. found 498.3.

Example 12

In Vitro Assay Against MenA

The enzymatic activity was determined by using membrane fractions prepared from *M. tuberculosis*. Reaction mixtures contained 5 mM MgCl$_2$, 0.1% CHAPS, 5 μM farnesyl diphosphate, and 50 μM dihydroxynaphthoic acid in 100 mM MOPS (pH 8.5). Various compounds of the present invention were added at various concentrations and IC$_{50}$ values were determined using Grafit 5.0.

Example 13

Activity Against *M. Tuberculosis*

The minimum inhibitory concentration (MIC) of compounds were determined against H37Rv by a colorimetric microtiter plate based method with Alamar blue. Some of the compounds of the present invention and the corresponding IC$_{50}$ aid MIC are shown in Table 1A.

TABLE 1A

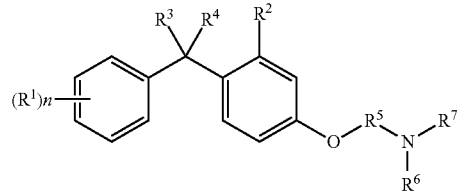

Representative compounds of Formula A and the corresponding activities

| Cpd | n | R$^1$ | R$^2$ | R$^3$, R$^4$ | R$^5$ | R$^6$ | R$^7$ | IC$_{50}$ (μmol) MenA | MIC (μg/mL) *M. tuberculosis* |
|---|---|---|---|---|---|---|---|---|---|
| 1 | 1 | 4-Br | H | O | —(CH$_2$)$_7$— | Me | Allyl | 12 | 5 |
| 2 | 1 | 4-Br | H | O | —(CH$_2$)$_8$— | Me | Allyl | 10 | 4 |
| 3 | 1 | 4-Br | H | H, OH | —(CH$_2$)$_7$— | Me | Allyl | 15 | 5 |
| 4 | 1 | 4-Br | H | H, OH | —(CH$_2$)$_8$— | Me | Allyl | 12 | 7 |
| 5 | 1 | 4-Cl | H | O | —(CH$_2$)$_8$— | Me | Allyl | 5 | 0.3 |
| 6 | 1 | 4-Cl | H | H, OH | —(CH$_2$)$_8$— | Me | Allyl | 10 | 3 |
| 7 | 2 | 2,4-Cl | H | O | —(CH$_2$)$_8$— | Me | Allyl | 10 | 4 |
| 8 | 2 | 2,4-Cl | H | H, OH | —(CH$_2$)$_8$— | Me | Allyl | 12 | 5 |
| 9 | 1 | 4-Cl | Cl | O | —(CH$_2$)$_8$— | Me | Allyl | 4 | 0.6 |
| 10 | 1 | 4-Cl | Cl | H, OH | —(CH$_2$)$_8$— | Me | Allyl | <2.5 | 0.6 |

TABLE 1A-continued

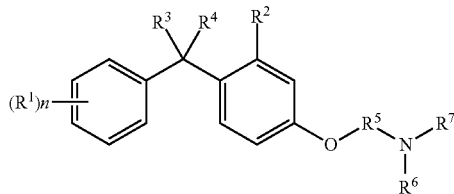

Representative compounds of Formula A and the corresponding activities

| Cpd | n | $R^1$ | $R^2$ | $R^3, R^4$ | $R^5$ | $R^6$ | $R^7$ | $IC_{50}$ (μmol) MenA | MIC (μg/mL) M. tuberculosis |
|---|---|---|---|---|---|---|---|---|---|
| 11 | 1 | 4-Cl | Cl | O | —(CH$_2$)$_8$— | Me | —CH$_2$C≡CH | 15 | 12 |
| 12 | 1 | 4-Cl | Cl | O | —(CH$_2$)$_8$— | Me | —CH$_2$Ph | 13 | 12 |
| 13 | 1 | 4-Cl | OH | O | —(CH$_2$)$_8$— | Me | Allyl | <2.5 | 0.2 |

Example 14

Various compounds of the invention were tested and their MIC was determined against a battery of M. tuberculosis strains (Table 2) as well as other bacteria (Table 3). As can be seen in Table 3, compounds of the invention are active against various species of bacteria. It appears that gram-positive bacteria growth was particularly susceptible to compounds of the invention. Without being bound by any theory, this is believed to be due to inhibition of menaquinone synthesis by the compounds of the invention.

Interestingly, growth of drug resistant Gram-positive organisms, including MRSA and MRSE, were sensitive to the compounds of the invention. Accordingly, it is believed that inhibition of menaquinone synthesis is a valid means for treating Gram-positive organisms.

TABLE 2

Minimum inhibitory concentrations (MIC) (μg/ml) of Compounds 20, 21 and 22 of the invention and Rifampicin (RFP) and isoniazid (INH) against Mycobacterium species determined using the agar (7H11) dilution method.

| Bacterium | RFP | INH | Cpd #20 | Cpd #21 | Cpd #22 |
|---|---|---|---|---|---|
| M. tuberculosis H37Rv | 0.2 | 0.1 | 6.25 | 25 | 1.56 |
| M. tuberculosis H37Rv | 0.1 | 0.1 | 6.25 | 25 | 1.56 |
| M. tuberculosis H37Rv | 0.2 | >25 | 6.25 | 12.5 | 1.56 |
| M. tuberculosis H37Rv | >25 | 0.05 | 6.25 | 25 | 1.56 |
| M. tuberculosis H37Rv | 0.2 | 0.1 | 6.25 | 25 | 3.13 |
| M. tuberculosis Kurono | 0.1 | 0.05 | 6.25 | 25 | 1.56 |
| M. bovis BCG Tokyo | 0.1 | 0.1 | 6.25 | 25 | 3.13 |
| M. avium Flamingo | 3.13 | >25 | 12.5 | >25 | 6.25 |
| M. intracellularae ATCC 15984 | 3.13 | 12.5 | 12.5 | >25 | 6.25 |
| M. kansasii NIHJ1619 | 3.13 | 12.5 | 12.5 | >25 | 6.25 |
| M. aurum | 0.78 | 6.25 | 12.5 | >25 | 6.25 |
| M. fortuitum NIHJ1615 | >25 | 6.25 | >25 | >25 | 12.5 |
| M. smegmatis Takeo | >25 | 12.5 | 25 | >25 | 12.5 |

TABLE 3

Minimum inhibitory concentrations (μg/ml) of Compounds 20, 21 and 22 of the invention, and Rifampicin (RFP) and isoniazid (INH) against Mycobacterium species determined using the agar (7H11) dilution method.

| Test Organism (Inoculum Size 106 CFU/ml) | MIC (μg/ml) | | | | | |
|---|---|---|---|---|---|---|
|  | Cpd #20 | Cpd #21 | Cpd #22 | DMPPC | VCM | OFLX |
| S. aureus ATCC 29213 | 25 | 100 | 25 | 1.56 | 0.78 | 0.2 |
| S. aureus ATCC 43300 (MRSA) | 25 | 100 | 25 | 3.13 | 0.78 | 0.39 |
| VRSA 2441-T0041 | 50 | >100 | 25 | >400 | 3.13 | 1.25 |
| VRSA 2441-T0044 | 50 | >100 | 25 | >400 | 6.25 | 1.25 |
| MRSA 2441-05104 | 25 | 50 | 25 | 100 | 0.78 | 25 |
| MRSA 2441-05112 | 25 | >100 | 25 | 400 | 0.78 | 50 |
| MRSA 2441-05129 | 25 | >100 | 50 | >400 | 0.78 | 1.00 |
| MRSA 2441-05223 | 25 | >100 | 25 | 125 | 0.78 | 0.2 |
| MRSA 2441-05254 | 25 | >100 | 50 | >400 | 1.56 | 50 |
| MRSA 2441-05262 | 25 | 100 | 25 | >400 | 0.78 | 50 |
| S. epidermidis ATCC 12228 | 25 | 50 | 12.5 | 1.56 | 1.56 | 0.2 |

TABLE 3-continued

Minimum inhibitory concentrations (μg/ml) of Compounds 20, 21 and 22 of the invention, and Rifampicin (RFP) and isoniazid (INH) against *Mycobacterium* species determined using the agar (7H11) dilution method.

| Test Organism (Inoculum Size 106 CFU/ml) | MIC (μg/ml) | | | | | |
|---|---|---|---|---|---|---|
| | Cpd #20 | Cpd #21 | Cpd #22 | DMPPC | VCM | OFLX |
| MRSE 2442-05030 | 12.5 | 50 | 12.5 | 1.56 | 3.13 | 6.25 |
| MRSE 2442-05047 | 12.5 | 50 | 12.5 | 400 | 1.56 | 6.25 |
| MRSE 2442-05053 | 12.5 | 50 | 12.5 | 3.13 | 1.56 | 6.25 |
| MRSE 2442-05060 | 12.5 | 50 | 12.5 | 200 | 1.56 | 6.25 |
| MRSE 2442-05110 | 12.5 | 50 | 12.5 | 3.13 | 1.56 | 6.25 |
| MRSE 2442-05118 | 12.5 | 50 | 12.5 | 200 | 1.56 | 6.25 |
| *E. faecalis* ATCC 29212 | 12.5 | 100 | 12.5 | 25 | 3.13 | 1.56 |
| *E. faecalis* ATCC 51299 (VRE) | 25 | >100 | 12.5 | 50 | 1.25 | 1.56 |
| *E. faecalis* NCTC 12201 (VRE) | 12.5 | 100 | 12.5 | 100 | >100 | 1.56 |
| *E. faecium* ATCC 49224 | 12.5 | 50 | 12.5 | >400 | 3.13 | 3.13 |
| *E. faecium* NCTC 12203 (VRE) | 12.5 | 50 | 6.25 | >400 | >100 | 3.13 |
| *E. coli* ATCC 25922 | >100 | >100 | 50 | >400 | >100 | 0.05 |
| *K. pneumoniae* ATCC 27736 | >100 | >100 | >100 | >400 | >100 | 0.2 |
| *P. mirabilis* ATCC 4630 | >100 | >100 | >100 | >400 | >100 | 0.39 |
| *S. marsascens* ATCC 14756 | >100 | >100 | >100 | >400 | >100 | 0.024 |
| *P. aeruginosa* ATCC 27853 | >100 | >100 | >100 | >400 | >100 | 3.13 |

VRSA 2441-T0041 & T0044, Low level VCM-resistant. *E. faecalis* ATCC 51299 (VRE), Low level VCM-resistant, Van B. *E. faecalis* NCTC 12201 (VRE), High level VCM-resistant, Van A. *E. faecium* NCTC 12203 (VRE), High level VCM-resistant, Van A. *E. faecium* ATCC 49224, GM-resistant.

Example 15

One of the goals of TB drug development is to find a drug to have activity against human latent tuberculosis infection (LTBI) since a large number of active tuberculosis cases arise from reactivation. Without being bound by any theory, it is generally believed that in LTBI, oxygen tension in the granuloma is low due to encapsulation and calcification of the lesion, which in turn results in bacterial dormancy. Inhibition of menaquinone synthesis by compounds of the invention showed a substantial effect on entrance to, and maintenance of dormancy in M tuberculosis. It is believed that MenA inhibitors are able to block the electron flow without inducing a dormancy response in *M. tuberculosis*. Accordingly, bacteria will likely behave as though they are in aerobic conditions even when treated with a MenA inhibitor.

The effectiveness of compounds 20 and 22 of the invention was tested against dormant bacteria using an in vitro assay of *M. tuberculosis* grown under low oxygen conditions using modified procedure of Wayne et al., "An in vitro model for sequential study of shiftdown of *Mycobacterium tuberculosis* through two stages of nonreplicating persistence," *Infect, Immun.* 1996, 64, 2062-2069. Briefly, an aerobic preculture was diluted 100-fold (from an $OD_{600}=0.5$ pre-culture) in tubes closed with rubber septa to ensure the anaerobic growth of the bacteria. Tubes were incubated on stirring platforms at 150 rpm (taking care that the surface layer was not disturbed). Compounds were deoxygenated by purging with nitrogen and were subsequently added by injection through the septa. Drug exposure lasted for about 96 h, after which the bacterial suspension was diluted and plated. Plates were then grown aerobic-ally at 37° C. and colonies were counted. The results (summarized in Table 4) indicate that the compounds of the invention are highly active against, non-replicating bacilli in low oxygen conditions.

TABLE 4

| Compound | (μg/mL) | CFU/mL Day 24 | Log10 CFU/mL Day 24 | SEM | % Growth v. Control Activity Day 24 | Day 24 |
|---|---|---|---|---|---|---|
| Control | NA | 1.08E+07 | 7.03 | 0.04 | 100.0% | NA |
| INH | 10 | 5.13E+06 | 6.65 | 0.17 | 46.450% | |
| RIF | 10 | 9.38E+04 | 4.92 | 0.14 | 0.868% | Highly Active |
| ETHAM | 10 | 9.14E+06 | 6.96 | 0.01 | 84.629% | |
| #20 | 10 | 3.05E+06 | 6.37 | 0.33 | 28.210% | |
| #20 | 50 | 9.38E+04 | 4.96 | 0.12 | 0.868% | Highly Active |
| #22 | 10 | 2.84E+04 | 4.32 | 0.35 | 0.263% | Highly Active |
| #22 | 50 | 6.05E+01 | 1.04 | 1.04 | 0.001% | Highly Active |

The results are presented in the table as % surviving bacteria after treatment with the compound versus the untreated controls (which are represented as 100%).
Scoring of activity is as follows:
drug treated cultures with 2-20% growth v. untreated controls: ACTIVE
drug treated cultures with <2% growth v. untreated controls: HIGHLY ACTIVE Several compounds were highly active at 50 μg/mL (not all the data shown). Some compounds were highly active at both high and low concentrations, 10 and 50 μg/mL, respectively (not all the data shown). The controls gave results that would be consistent with a low-oxygen model: rifampin (RIF) was highly active, while isoniazid (INH) and ethambutol (ETHAM) showed a lesser amount of killing activity.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure, it is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter. All references disclosed herein are incorporated by reference in their entirety.

What is claimed:

1. A compound of the Formula:

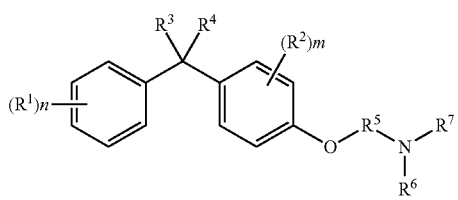

or a pharmaceutically acceptable salt thereof,
wherein:
  m is an integer from 0 to 4;
  n is an integer from 0 to 5;
  each of $R^1$ and $R^2$ is independently bromine, chlorine, haloalkyl, or —$OR^8$;
  each of $R^3$ and $R^4$ is independently hydrogen or —$OR^8$;
  or $R^3$ and $R^4$ together form =X, wherein X is O, S, or $NR^9$;
  $R^5$ is a linker having from 8 to 12 atoms, each of which is independently selected from the group consisting of C, N, O, S, provided no two heteroatoms are adjacent to one another, forming a substituted or unsubstituted alkylene, alkenylene, or alkynylene;
  $R^6$ is hydrogen, alkyl, or —$NR^{10}R^{11}$;
  each of $R^7$ and $R^{10}$ is independently hydrogen, alkyl, aralkyl, alkenyl, or alkynyl;
  each of $R^8$ and $R^9$ is independently hydrogen or alkyl; and $R^{11}$ is hydrogen or alkyl,
wherein one of $R^3$ and $R^4$ is hydrogen and the other is —$OR^8$.

2. A compound of the Formula:

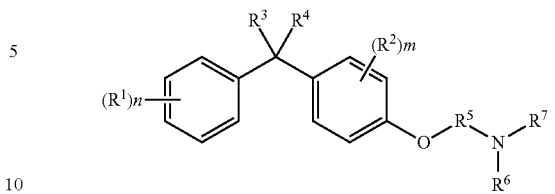

or a pharmaceutically acceptable salt thereof,
wherein:
  m is an integer from 0 to 4;
  n is an integer from 0 to 5;
  each of $R^1$ and $R^2$ is independently bromine, chlorine, haloalkyl, or —$OR^8$;
  each of $R^3$ and $R^4$ is independently hydrogen or —$OR^8$;
  or $R^3$ and $R^4$ together form =X, wherein X is O, S, or $NR^9$;
  $R^5$ is a linker having from 8 to 12 atoms, each of which is independently selected from the group consisting of C, N, O, S, provided no two heteroatoms are adjacent to one another, forming a substituted or unsubstituted alkylene, alkenylene, or alkynylene;
  $R^6$ is hydrogen, alkyl, or —$NR^{10}R^{11}$;
  each of $R^7$ and $R^{10}$ is independently hydrogen, alkyl, aralkyl, alkenyl, or alkynyl;
  each of $R^8$ and $R^9$ is independently hydrogen or alkyl; and $R^{11}$ is hydrogen or alkyl,
wherein $R^5$ is a substituted alkylene, alkenylene or alkynylene, substituted with one or more halogens.

3. A compound selected from the group consisting of compounds 14 through 18 and 20 through 22 shown in Table 1:

TABLE 1

Representative compounds of Formula A and the corresponding activities

| Cpd | n | $R^1$ | $R^2$ | $R^3, R^4$ | $R^5$ | $R^6$ | $R^7$ |
|---|---|---|---|---|---|---|---|
| 1 | 1 | 4-Br | H | O | —$(CH_2)_7$— | Me | Allyl |
| 2 | 1 | 4-Br | H | O | —$(CH_2)_8$— | Me | Allyl |
| 3 | 1 | 4-Br | H | H, OH | —$(CH_2)_7$— | Me | Allyl |
| 4 | 1 | 4-Br | H | H, OH | —$(CH_2)_8$— | Me | Allyl |
| 5 | 1 | 4-Cl | H | O | —$(CH_2)_8$— | Me | Allyl |
| 6 | 1 | 4-Cl | H | H, OH | —$(CH_2)_8$— | Me | Allyl |
| 7 | 2 | 2,4-Cl | H | O | —$(CH_2)_8$— | Me | Allyl |
| 8 | 2 | 2,4-Cl | H | H, OH | —$(CH_2)_8$— | Me | Allyl |
| 9 | 1 | 4-Cl | Cl | O | —$(CH_2)_8$— | Me | Allyl |
| 10 | 1 | 4-Cl | Cl | H, OH | —$(CH_2)_8$— | Me | Allyl |
| 11 | 1 | 4-Cl | Cl | O | —$(CH_2)_8$— | Me | —$CH_2C{\equiv}CH$ |
| 12 | 1 | 4-Cl | Cl | O | —$(CH_2)_8$— | Me | —$CH_2Ph$ |
| 13 | 1 | 4-Cl | OH | O | —$(CH_2)_8$— | Me | Allyl |
| 14 | | | | | —$(CH_2)_4$—O—$(CH_2)_3$— | | |
| 15 | | | | | —$CH_2$—CH=CH—$CH_2$—O—$(CH_2)_3$— | | |
| 16 | | | | | —$(CH_2)_5$—C≡C—$CH_2$— | | |
| 17 | | | | | —$(CH_2)_4$—O—$(CH_2)_3$— | —$NR^{10}R^{11}$ | H |
| 18 | | | | | —$CH_2$—CH=CH—$CH_2$—O—$(CH_2)_3$— | —$NR^{10}R^{11}$ | H |
| 19 | | | | | —$(CH_2)_5$—C≡C—$CH_2$— | —$NR^{10}R^{11}$ | H |
| 20 | 1 | 4-Cl | 2-Cl | O | —$(CH_2)_8$— | Me | Allyl |
| 21 | 1 | 4-Cl | 2-Cl | H, OH | —$(CH_2)_8$— | Me | Allyl |
| 22 | 1 | 4-Cl | 2-OH | O | —$(CH_2)_8$— | Me | Allyl. |

* * * * *